(12) United States Patent
Lupton (10) Patent No.: US 8,764,684 B2
(45) Date of Patent: *Jul. 1, 2014

(54) GUIDE WIRE FOR USE WITH A CATHETER

(71) Applicant: Brivant Research & Development Limited, Galway (IE)

(72) Inventor: Henry William Lupton, Galway (IE)

(73) Assignee: Brivant Research & Development Limited, Galway (IE)

(*) Notice: Subject to any disclaimer, the term of this patent is extended or adjusted under 35 U.S.C. 154(b) by 0 days.

This patent is subject to a terminal disclaimer.

(21) Appl. No.: 13/958,903

(22) Filed: Aug. 5, 2013

(65) Prior Publication Data

US 2013/0317482 A1 Nov. 28, 2013

Related U.S. Application Data

(63) Continuation of application No. 10/539,399, filed as application No. PCT/IE03/00173 on Dec. 19, 2003, now Pat. No. 8,500,656.

(30) Foreign Application Priority Data

Dec. 20, 2002 (IE) .................................. S2002/0988

(51) Int. Cl.
 *A61M 25/00* (2006.01)
 *A61M 5/178* (2006.01)

(52) U.S. Cl.
 USPC ...................................... 600/585; 604/164.13

(58) Field of Classification Search
 USPC .............................. 600/434, 585; 604/164.13
 See application file for complete search history.

(56) References Cited

U.S. PATENT DOCUMENTS 5,095,915 A * 3/1992 Engelson ...................... 600/585
5,135,503 A * 8/1992 Abrams ..................... 604/164.13
5,203,772 A * 4/1993 Hammerslag et al. ........ 604/528
5,365,942 A * 11/1994 Shank ........................... 600/585
5,772,609 A * 6/1998 Nguyen et al. ................ 600/585
7,083,577 B2 * 8/2006 Osawa et al. ................. 600/585
8,500,656 B2 * 8/2013 Lupton ......................... 600/585
2002/0062092 A1 5/2002 Muni et al.

FOREIGN PATENT DOCUMENTS

WO 92/08510 5/1992

OTHER PUBLICATIONS

International Search Report for PCT App. No. PCT/IE03/00173 mailed on Mar. 3, 2004.

* cited by examiner

*Primary Examiner* — Max Hindenburg
*Assistant Examiner* — John Pani
(74) *Attorney, Agent, or Firm* — Whyte Hirschboeck Dudek SC; Grady J. Frenchick (57) ABSTRACT

A guide wire (1) for use with a catheter comprises a core wire (3) terminating in a distal portion (18) of flat ribbon-like construction having respective opposite major surfaces (29, 30). A spring (24) is brazed to a distal end (27) of the distal portion (18) and to the core wire (3) at a tapering portion (14). A reinforcing member (38) extends axially along the distal portion (18) from a proximal end (26) of the distal portion (18) to a location (40) for reinforcing the distal portion (18) for in turn increasing its torsional rigidity in order to minimise axial twisting of the distal portion (18). A guide portion (42) of the distal portion (18) between the location (40) and the distal end (27) is provided to be bent at a desired set curved configuration for offsetting a distal tip (9) of the guide wire (1) from a central axis (8) thereof, so that by rotating the guide wire (1) at its proximal end (5) the distal portion (18) is also rotated for aligning the distal tip (9) with a branched vessel into which it is desired to direct and urge the guide wire (1).

1 Claim, 6 Drawing Sheets

GUIDE WIRE FOR USE WITH A CATHETER

The present invention relates to a guide wire for use in a surgical or other procedure for accessing a remote site in the body of a human or animal subject, and in particular though not limited to a guide wire for use with a catheter.

Guide wires for locating a distal end of a catheter in a remote site in the body of a human or animal subject are known. Such guide wires are commonly used for guiding a catheter along narrow blood vessels to a site in the cardiovascular system of the subject for enabling a cardiovascular procedure to be carried out, for example, the insertion of a stent in a coronary artery. Depending on the type of guide wire and its use, the guide wire is typically introduced through a cannula into a suitable blood vessel in the thigh, arm or neck of the subject, and is passed through the blood vessels to the desired site in the cardiovascular or other system. In cases where a guide wire is for use with a catheter for inserting a stent in a coronary artery of the heart of a subject, the guide wire may be introduced through a guide catheter, and through the guide catheter to the coronary artery. Once the guide wire has reached the desired site, the appropriate catheter is then advanced over the guide wire to the site.

Due to the relatively narrow diameter of the blood vessels through which a guide wire has to pass, and in particular, due to the tortuous nature of the blood vessels, and particularly the tortuous nature of the blood vessels of the cardiovascular system, and the number of branched blood vessels, it is essential that the guide wire be of a construction which facilitates bending of the guide wire so that the guide wire can bend around corners, and additionally, it is essential that the guide wire can be selectively directed into branched blood vessels. In order to facilitate bending of the guide wire around corners, such guide wires are provided to be relatively flexible, and the desired flexibility, in general, is obtained by selecting the material and dimensions of the guide wire to provide the desired degree of flexibility. In order that such guide wires can be directed into a branched blood vessel, a distal portion of the guide wire is adapted to be bent to a set curved configuration, and to retain the set curved configuration as the guide wire is being urged through the vascular system. As the guide wire is being urged through the vascular system, when it is desired to direct the guide wire into a branched vessel, the guide wire is rotated in order to align the distal tip of the guide wire with the branched vessel, and once aligned with the branched vessel, further forward urging of the guide wire directs the guide wire into the branched vessel. Accordingly, in order that the distal tip of the guide wire can be directed towards and aligned with a branched vessel, it is important that the guide wire be torsionally rigid over its length, otherwise axial twisting of the guide wire occurs between the distal end and the proximal end, since rotation of the guide wire must be undertaken by rotating the proximal end of the guide wire.

In general, by appropriately selecting the material and dimensions of the guide wire, the required degree of torsional rigidity can be obtained relatively easily over most of the guide wire. However, in general a greater degree of flexibility is required towards the distal end of the guide wire, and in order to provide the extra degree of flexibility and to facilitate bending of the guide wire into a desired set curved configuration adjacent the distal end, in general, such guide wires are provided with a tapered portion adjacent the distal end. Such a guide wire is disclosed in U.S. Pat. No. 4,545,390 of Leary. While the provision of the tapered distal portion provides the additional degree of flexibility, and also lends itself readily to being bent to form a desired set curved configuration, unfortunately, the tapering of the guide wire at the distal portion significantly reduces the torsional rigidity of the guide wire in the distal portion. Thus, while the guide wire over the majority of its length is adequately torsionally rigid, the distal portion has little or no torsional rigidity, and thus, significant twisting can occur in the tapered distal portion between the proximal end and the distal tip of the guide wire. This leads to significant difficulty in aligning the distal tip of the guide wire with a selected branched vessel by rotating the guide wire at its proximal end.

In order to improve the torsional rigidity of the tapered distal portion of the guide wire of Leary in U.S. Pat. No. 4,545,390, a sleeve formed by a tightly wound coiled spring is provided, and the tapered distal portion is located coaxially within the tightly coiled spring. The spring is secured to the distal end of the distal portion and is also secured to the guide wire intermediate the tapered distal portion and the proximal end. However, while the provision of the tightly wound coiled spring extending around the tapered distal portion does to some extent enhance the torsional rigidity of the distal portion, the degree of enhancement of the torsional rigidity is limited, and axial twisting of the guide wire occurs between the proximal end and the distal tip.

U.S. Pat. No. 4,080,706 of Heilman discloses a guide wire comprising a main wire which extends between a proximal end and a distal end of the guide wire, and which is located within a tightly wound coiled spring sleeve. A distal portion of the guide wire is flattened and tapered to form a ribbon-like portion which increases the degree of flexibility of the guide wire adjacent the distal end thereof. However, the flattened ribbon-like distal portion of the main wire has little torsional rigidity, and the provision of the tightly wound coiled spring sleeve would add little to the torsional rigidity of the guide wire adjacent the ribbon-like distal portion of the main wire. Thus, if one were to form a set curved configuration in the flattened ribbon-like distal portion of the guide wire of Heilman in order to facilitate alignment of the distal tip of the guide wire with a branched vessel, the lack of torsional rigidity of the distal portion of the guide wire would render alignment of the distal tip of the guide wire with the branched vessel virtually impossible. Due to the lack of torsional rigidity of the flattened ribbon-like distal portion of the main wire, rotation of the proximal end of the guide wire would merely lead to twisting of the flattened ribbon-like distal portion, thereby rendering it impossible to align the distal tip of the guide wire with a branched vessel by rotating the guide wire at its proximal end.

There is therefore a need for a guide wire which is sufficiently flexible to facilitate bending of the guide wire around corners and bends in the vascular system, and which also is provided with a distal portion which is adapted to be bent to a set curved configuration, and which is sufficiently torsionally rigid to prevent axial twisting of the guide wire between the distal end of the guide wire and the proximal end thereof so that rotation of the guide wire adjacent its proximal end results in a corresponding degree of rotation of the guide wire adjacent its distal tip.

The present invention is directed towards providing such a guide wire.

According to the invention there is provided a guide wire for use in a surgical or other procedure for accessing a remote site in the body of a human or animal subject, the guide wire defining a longitudinally extending axis, and terminating at one end in a proximal portion, and at an opposite end in a distal portion for accessing the remote site, the distal portion terminating adjacent a distal end thereof in a guide portion, the guide portion being adapted to be shaped to a desired curved configuration for facilitating guiding of the guide wire into a branched vessel of the subject, wherein a reinforcing means is provided on the distal portion for minimising axial twisting of the distal portion between a proximal end of the distal portion and the guide portion thereof.

In one embodiment of the invention the reinforcing means is an elongated reinforcing means having a proximal end and a distal end. Preferably, the reinforcing means extends along at least a portion of the distal portion between the proximal end of the distal portion and the guide portion. Advantageously, the distal end of the reinforcing means is spaced apart from the distal end of the distal portion of the guide wire and defines with the distal end of the distal portion of the guide wire the guide portion thereof. Ideally, the reinforcing means extends from the proximal end of the distal portion, and preferably, the proximal end of the reinforcing means substantially coincides with the proximal end of the distal portion of the guide wire.

In one embodiment of the invention the reinforcing means extends in a generally axial direction.

In another embodiment of the invention the distal portion of the guide wire defines a longitudinally extending flat surface, and the reinforcing means extends along the flat surface and from the flat surface terminating in a longitudinally extending edge.

Preferably, the distal portion of the guide wire is of rectangular transverse cross-section defining a pair of opposite major flat surfaces, joined by a pair of opposite minor surfaces, the major flat surfaces defining a central major plane located midway between the major surfaces, and the minor surfaces defining a central minor plane located midway between the minor surfaces.

In one embodiment of the invention the reinforcing means is located on one of the major flat surfaces, and in another embodiment of the invention the reinforcing means is located on both of the major flat surfaces.

Advantageously, the respective major flat surfaces converge towards each other towards the distal end of the distal portion.

In one embodiment of the invention the transverse distance of the longitudinally extending edge of each reinforcing means from the central major plane is substantially constant along the reinforcing means.

In another embodiment of the invention each reinforcing means extends parallel to the central minor plane. Preferably, each reinforcing means coincides with the central minor plane. Alternatively, each reinforcing means extends at an angle greater than zero degrees to the central minor plane, and in one embodiment of the invention each reinforcing means extends adjacent one of the minor surfaces.

In one embodiment of the invention one reinforcing means extends from each of the major flat surfaces, one of the reinforcing means extending adjacent one of the minor surfaces, and the other reinforcing means extending adjacent the other minor surface.

In another embodiment of the invention each reinforcing means comprises an elongated reinforcing member. Preferably, each reinforcing member defines opposite longitudinally extending sides. Advantageously, the opposite longitudinally extending sides of each reinforcing member terminate along the longitudinally extending edge thereof, and preferably, the opposite longitudinally extending sides of each reinforcing member are parallel to each other. Alternatively, the opposite longitudinally extending sides of each reinforcing member converge towards the longitudinally extending edge thereof for defining the longitudinally extending edge as a longitudinally extending ridge.

In one embodiment of the invention the longitudinally extending edge of each reinforcing member converges towards the distal portion adjacent the distal end of to the reinforcing member.

In another embodiment of the invention each reinforcing means is integrally formed with the distal portion.

In a further embodiment of the invention each reinforcing means and the distal portion are of metal and are formed by forging from a single piece of metal. Alternatively, each reinforcing means and the distal portion are of metal and are formed by rolling from a single piece of metal.

In one embodiment of the invention the distal portion of the guide wire extends through a sleeve, and a first securing means at the distal end thereof secures the distal portion to the sleeve, the first securing means defining the distal end of the guide wire. Preferably, the first securing means is shaped to form a dome shaped distal end for facilitating passage of the guide wire smoothly through a vessel of the subject. Advantageously, the guide portion is located between each reinforcing means and the first securing means.

In one embodiment of the invention the first securing means comprises a solder joint. Alternatively, the first securing means comprises an adhesive joint, or alternatively, the first securing means comprises a brazed joint.

In one embodiment of the invention the sleeve extends beyond the proximal end of the distal portion along a portion of the guide wire. Preferably, a proximal end of the sleeve is secured to the guide wire by a second securing means.

In one embodiment of the invention the second securing means comprises one of an adhesive joint, or a solder joint, or a brazed joint.

In another embodiment of the invention the sleeve is secured to the guide wire at at least one intermediate location intermediate the proximal end and the distal end of the sleeve by an intermediate securing means.

In a further embodiment of the invention the intermediate securing means comprises one of an adhesive joint, a solder joint, or a brazed joint.

In another embodiment of the invention at least a portion of the sleeve adjacent the distal end thereof is of a radiopaque material.

Preferably, the sleeve comprises a tightly wound coiled spring of a metal material. Additionally, or alternatively, the sleeve comprises a tubular member, and the tubular member may be of plastics material.

In another embodiment of the invention the sleeve is formed from alternate portions of the tightly wound coiled spring and the tubular member.

In a further embodiment of the invention at least a portion of the sleeve is formed from one or more of the following materials or alloys thereof:
platinum,
gold,
tantalum.

Preferably, the guide wire is substantially torsionally rigid between the distal portion and the proximal portion of the guide wire for minimising axial twisting of the guide wire between the proximal portion thereof and the guide portion.

In one embodiment of the invention a portion of the guide wire adjacent the distal portion thereof tapers towards the distal portion.

In another embodiment of the invention the distal portion of the guide wire and the guide wire are integrally formed from one piece of material.

The invention also provides a distal portion for a guide wire of the type for use in a surgical or other procedure for accessing a remote site in the body of a human or to animal subject, the guide wire defining a longitudinally extending axis, and the distal portion having a proximal end and a distal end, the proximal end of the distal portion being adapted for securing to the guide wire, the distal portion terminating in a guide portion adjacent the distal end thereof, the guide portion being adapted to be shaped to a desired curved configuration for facilitating guiding of the guide wire into a branched vessel of the subject, characterised in that a reinforcing means is provided on the distal portion for minimising axial twisting of the distal portion between a proximal end of the distal portion and the guide portion thereof.

The invention also provides in combination a catheter, and the guide wire according to the invention.

The advantages of the invention are many. The provision of the reinforcing means in the distal portion of the guide wire significantly increases the torsional rigidity of the distal portion, thereby any danger of axial twisting of the distal portion is minimised. By minimising axial twisting of the distal portion, provided the guide wire up to the distal portion is of adequate torsional rigidity, rotation of the guide wire at its proximal end results in rotation of the distal end through a corresponding angle to that through which the proximal end is rotated. Thus, when a desired curvature is formed in the guide portion of the distal portion, the distal tip of the guide wire can be readily directed towards and align with a branched vessel into which the guide wire is to be urged by rotating the proximal end of the guide wire through an appropriate angle for aligning the distal tip with the branched vessel. By locating the reinforcing means so that it extends from the proximal end of the distal portion to the guide portion, torsional rigidity of the distal portion is maintained over its length between its proximal end and the guide portion. The provision of the reinforcing means as an elongated reinforcing member which extends from a surface, and in particular a flattened major surface of the distal portion, further enhances the torsional rigidity of the distal portion. By locating the reinforcing member so that it substantially coincides with the central minor plane of the distal portion further enhances the torsional rigidity of the distal portion. When the distal portion is provided to be of rectangular cross-section with respective opposite major surfaces, the provision of the reinforcing means significantly enhances the torsional rigidity of the distal portion. Indeed, by providing the reinforcing means as an elongated reinforcing member, which preferably coincides with the central minor plane of the distal portion significantly enhances the torsional rigidity of the distal portion. The provision of a pair of reinforcing members, while not essential, on respective opposite major surfaces of the distal portion further enhances the torsional rigidity of the distal portion.

The invention will be more clearly understood from the following description of some preferred embodiments thereof, which are given by way of example only, with reference to the accompanying drawings, in which:

FIGS. 11(a) to (p) are transverse cross-sectional end elevational views similar to FIG. 4 of guide wires according to further different embodiment of the invention.

Referring to the drawings and initially to FIGS. 1 to 6 thereof, there is illustrated a guide wire according to the invention, indicated generally by the reference numeral 1, for use with a catheter (not shown) for guiding the catheter to a remote site in the body of a human or animal subject. The guide wire 1 according to this embodiment of the invention is particularly suitable for accessing a remote site, for example, a coronary artery in the cardiovascular system of a subject for in turn guiding a catheter to the remote site. Although it will be readily apparent to those skilled in the art that the guide wire 1 is suitable for accessing any remove site in the body, be it in a vasculature system or otherwise. For example, the guide wire 1 is suitable for accessing renal vessels, the neuro-vasculature system, the fallopian tubes, and other such vessels and sites.

Figure 1:
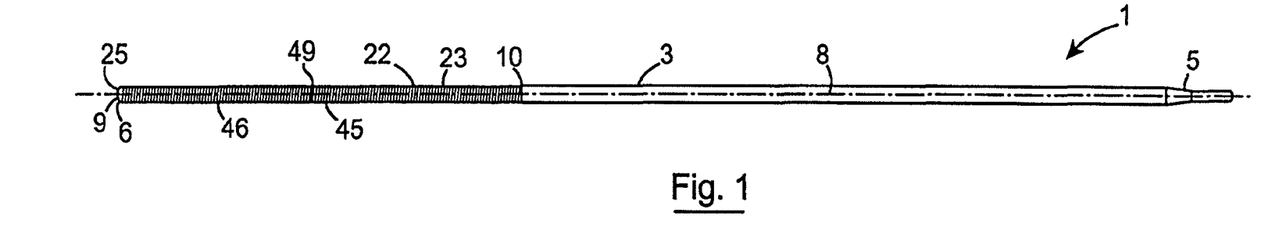
FIG. 1 is a side elevational view of a guide wire according to the invention.
Figures 2, 4:
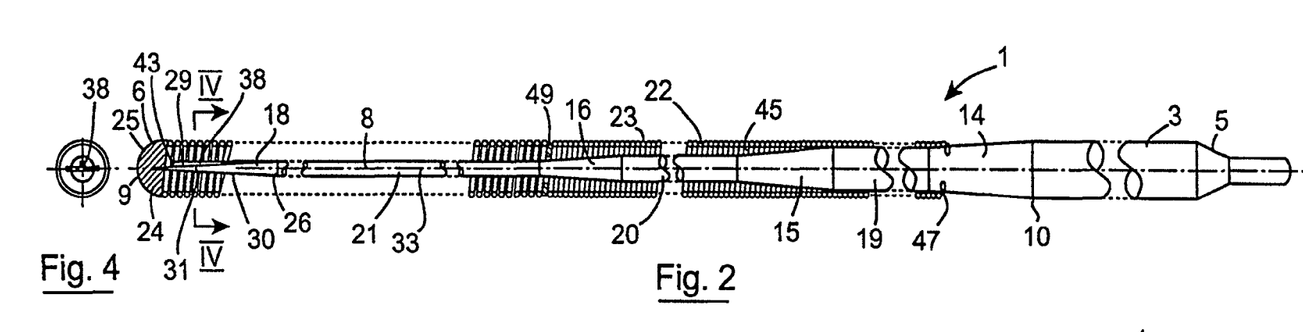
FIG. 2 is an enlarged partly cut away side elevational view of the guide wire of FIG. 1.
FIG. 4 is a transverse cross-sectional end elevational view of the guide wire of FIG. 1 on the line IV-IV of FIG. 2.
Figure 3:
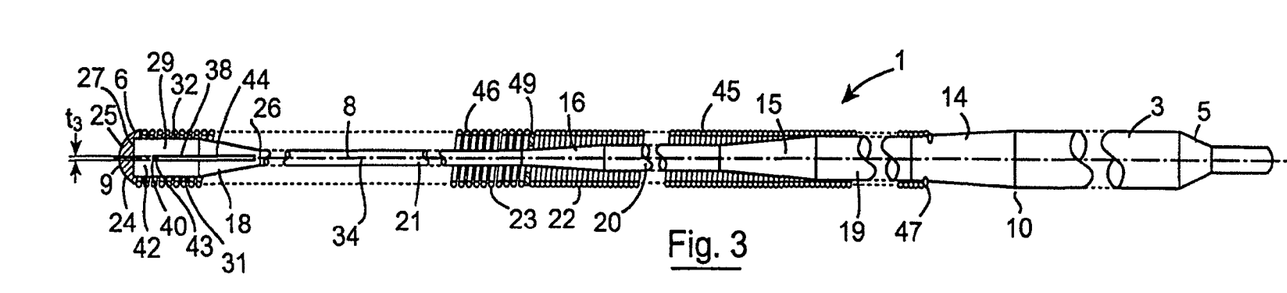
FIG. 3 is an enlarged partly cut away plan view of the guide wire of FIG. 1.

The guide wire 1 comprises an elongated core wire 3 of metal, in this embodiment of the invention stainless steel, which extends between a proximal end 5 and a distal end 6, and defines a longitudinally extending central axis 8. The distal end 6 of the guide wire 1 forms a distal tip 9 which in use forms the leading end of the guide wire 1 as it is urged through the blood vessels or other vessels in the subject to the remote site. The core wire 3 over most of its length from the proximal end 5 is of circular transverse cross-section of constant diameter in the range of 0.2 mm to 0.5 mm, and towards its distal end at a location 10 commences to taper towards the distal end 6. The core wire 3 tapers in multiple steps, in this embodiment of the invention three steps providing three tapering portions 14, 15 and 16 of circular transverse cross-section, between the location 10 and a distal portion 18 for increasing the flexibility of the guide wire 1 towards the distal end thereof. The tapering portions 14, 15 and 16 terminate in corresponding portions 19, 20 and 21, respectively, which are of circular transverse cross-section of constant diameter. The constant diameter portion 21 terminates in the distal portion 18. A sleeve 22 provided in this embodiment of the invention by a tightly wound coiled spring 23 of metal as will be described below extends from the tapering portion 14 to the distal end 6 of the guide wire 1, and is secured to the core wire 3 at the distal end 6 by a first securing means, in this embodiment of the invention by a first solder joint 24. The first solder joint 24 forms a dome shaped portion 25 which forms the distal tip 9 of the guide wire 1. The dome shaped portion 25 minimises any risk of trauma to a subject as the guide wire 1 is being urged through the vascular system.

The distal portion 18 extends from the portion 21 at a proximal end 26 to a distal end 27, and is flattened to be of ribbon-like construction defining a pair of opposite major surfaces 29 and 30 and opposite minor surfaces 31 and 32. The distal portion 18 tapers gradually from its proximal end 26 to its distal end 27 with the respective major surfaces 29 and 30 converging towards each other. The major surfaces 29 and 30 define a central major plane 33 located midway between the major surfaces 29 and 30, and the minor surfaces 31 and 32 define a central minor plane 34 midway between the minor surfaces 31 and 32, and perpendicular to the central major plane 33.

A reinforcing means comprising a reinforcing member 38 extends longitudinally along one of the major surfaces 29 and 30 of the distal portion 18 for increasing the torsional rigidity of the distal portion 18. In this embodiment of the invention the reinforcing member 38 extends along the major surface 29. The reinforcing member 38 coincides with the central minor plane 34, and extends axially along the major surface 29 from the proximal end 26 and terminates at 40. A guide portion 42 is defined in the distal portion 18 between the location 40 at which the reinforcing member 38 terminates and the first solder joint 24. The guide portion 42 of the distal portion 18 is provided without the reinforcing member 38 for facilitating bending of the guide portion 42 to a desired set curved configuration prior to entering the guide wire 1 into the vascular system of the subject, so that the distal tip 9 of the guide wire 1 can be offset from the central axis 8 for facilitating aligning of the distal tip 9 with a branched vessel of the vascular system, and guiding the guide wire 1 into a branched vessel during urging of the guide wire 1 through the vascular system of the subject.

In this embodiment of the invention the distal portion 18 and the reinforcing member 38 are integrally formed with the tapering portions 14, 15 and 16 and the constant diameter portions 19, 20 and 21, and with the core wire 3 by appropriately drawing, forging and/or rolling the core wire 3. Typically, the distal portion 18 is formed by forging or rolling, while the tapering portions 14, 15 and 16 and the constant diameter portions 19, 20 and 21 typically are formed by centreless grinding.

In this embodiment of the invention the axial length A of the distal portion 18 extending from the proximal end 26 to the distal end 27 is approximately 23 mm. The distal portion 18 tapers from a thickness $t_1$ of approximately 0.06 mm at its proximal end 26 to a thickness $t_2$ of approximately 0.02 mm at its distal end 27. The axial length C of the guide portion 42 is approximately 5 mm. The reinforcing member 38 extends for a length B of approximately 18 mm from the proximal end 26 to the location 40. The reinforcing member 38 is of rectangular transverse cross-section and defines opposite sides 37 which extend to a longitudinally extending edge 44. The reinforcing member 38 is of thickness $t_3$ of approximately 0.05 mm, and tapers at a portion 43 at its distal end towards the location 40 for an axial distance of approximately 0.05 mm. The distance d from the central major plane 33 to the longitudinally extending edge 44 of the reinforcing member 38 from the proximal end 26 to the commencement of the tapering portion 43 is substantially constant, and in this embodiment of the invention is approximately 0.03 mm. However, depending on the use to which the guide wire 1 is to be put, the axial length A of the distal portion 18 may vary between 13 mm and 25 mm, and the axial length C of the guide portion may vary between 4 mm and 8 mm. Additionally, the thickness $t_1$ of the distal portion 18 adjacent its proximal end may vary between 0.05 mm and 0.1 mm.

Returning now to the sleeve 22, the sleeve 22 is formed by the spring 23 which in this embodiment of the invention comprises a proximal spring 45 and a distal spring 46. Both springs 45 and 46 are tightly wound helical springs, the distal spring 46 being less tightly wound than the proximal spring 45 to increase the flexibility of the guide wire adjacent the distal portion 18. The proximal spring 45 is of stainless steel and is brazed to the core wire 3 at the tapering portion 14 by a second securing means, namely, by a second solder joint 47. The proximal and distal springs 45 and 46 are secured together by an intermediate securing means, namely, an intermediate solder joint 49. The intermediate solder joint 49 secures the proximal and distal springs 45 and 46 only together, and the springs 45 and 46 are free floating at the intermediate solder joint 49 relative to the core wire 3. The distal spring 46 is of a radiopaque material, in this embodiment of the invention platinum alloy.

Figure 5:
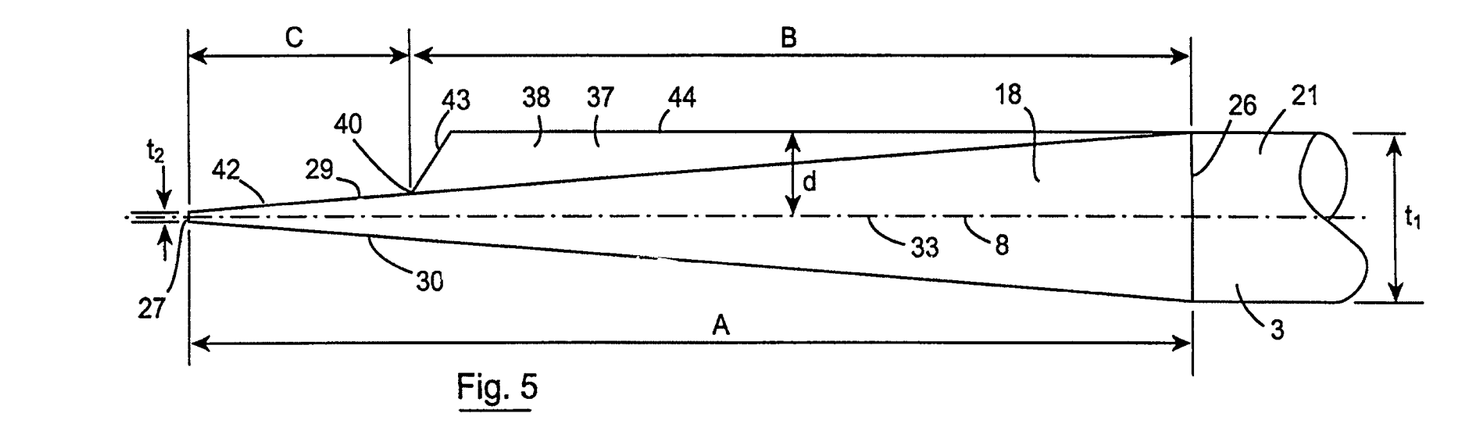
FIG. 5 is an enlarged side elevational view of the guide wire of FIG. 1 illustrating a portion only of the guide wire of FIG. 1.
Figure 6:
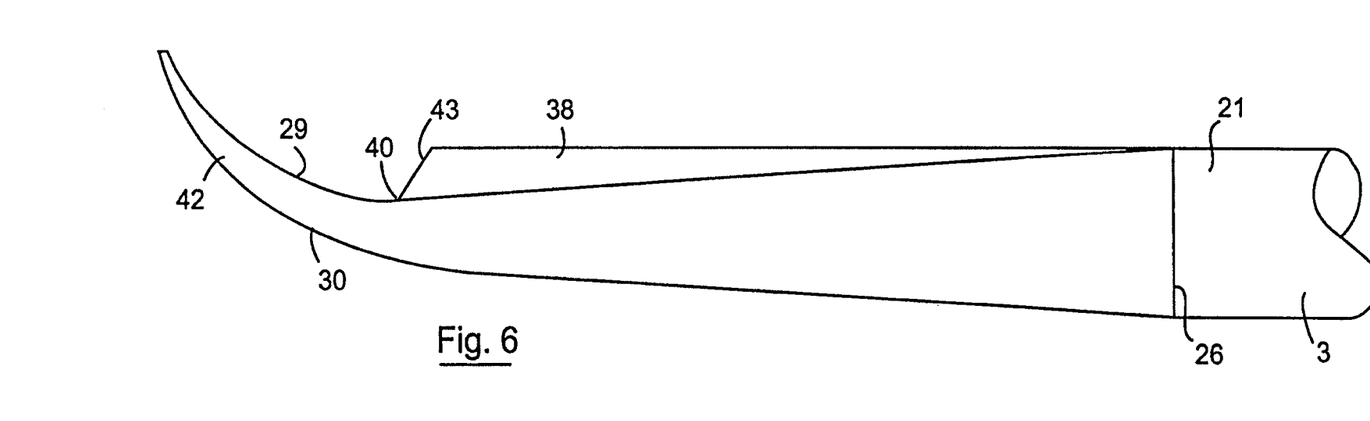
FIG. 6 is a side elevational view of the portion of the guide wire of FIG. 5 in a different configuration.

In use, prior to entering the guide wire 1 into the vascular system of a subject, the guide portion 42 of the distal portion 18 is bent to a desired set curved configuration for facilitating guiding and directing the guide wire 1 into branched vessels. Once bent, the guide portion 42 retains the set curved configuration during use of the guide wire 1. The guide wire 1 is then entered into the vascular system of the subject, and when it is desired to enter the guide wire 1 into a branched vessel, the guide wire 1 is rotated about its axis by rotating the proximal end 5 of the guide wire 1 until the distal tip 9 is directed towards and aligned with the branched vessel into which the guide wire 1 is to be entered. The guide wire 1 is then urged further into the vascular system so that the distal tip 9 enters the branched vessel, and further urging of the guide wire 1 into the vascular system urges the guide wire 1 through the branched vessel, and so on until the distal tip 9 of the guide wire is at the remote site at which the surgical procedure is to be carried out.

By virtue of the fact that the reinforcing member 38 is provided on the distal portion 18 from its proximal end 26 to the location 40 adjacent the guide portion 42, axial twisting of the distal portion 18 is substantially avoided, and accordingly, each incremental angular rotation of the guide wire 1 at the proximal end 5 results in a corresponding incremental angular rotation of the distal end 6 of the guide wire 1, and thus, when the guide portion 42 is bent to a desired set curved configuration, the distal tip 9 can readily easily be aligned with a branched vessel into which the guide wire 1 is to be urged.

Figure 7A:
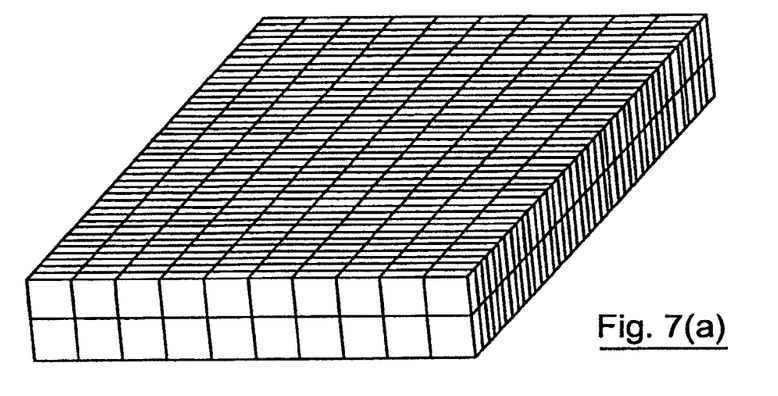
FIGS. 7(a) and 7(b), and 8(a) and 8(b) are perspective views of a reference piece and a test piece representing a portion of the guide wire of FIG. 1 during comparative finite element analysis.
Figure 7B:
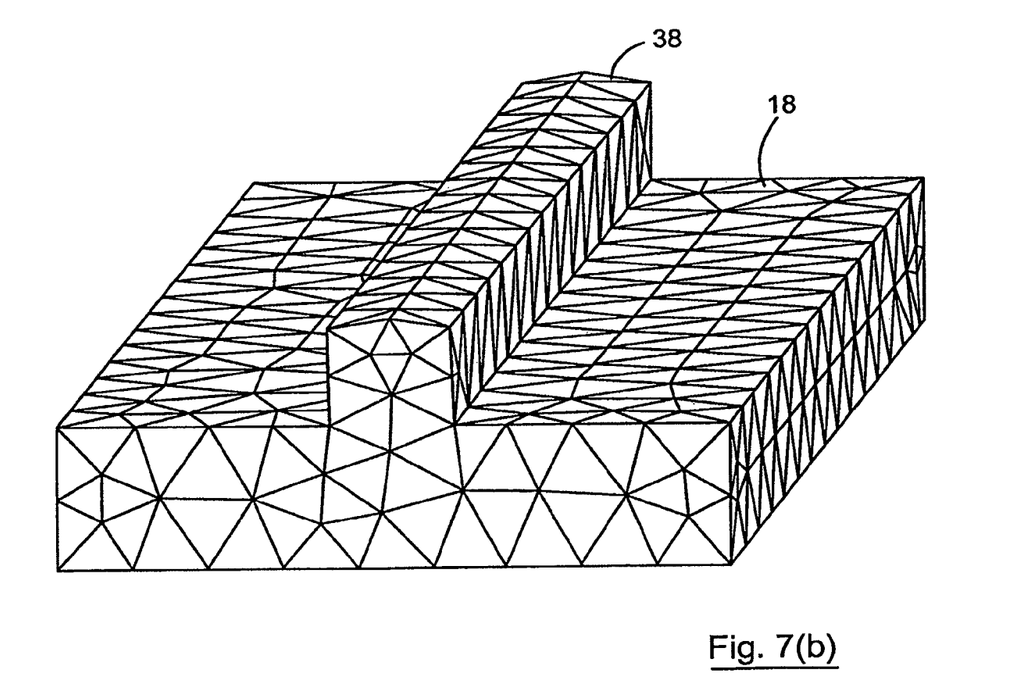
Figure 8A:
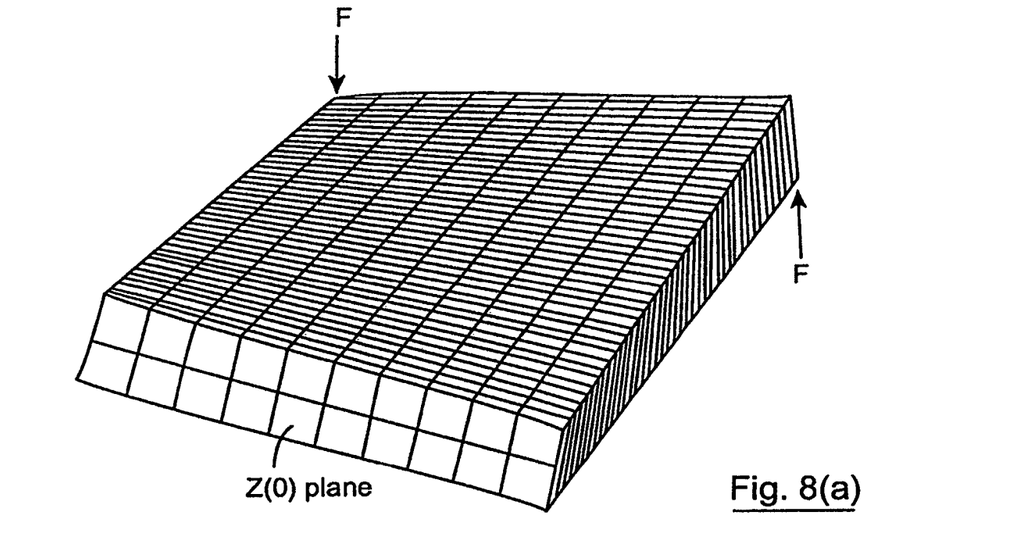
Figure 8B:
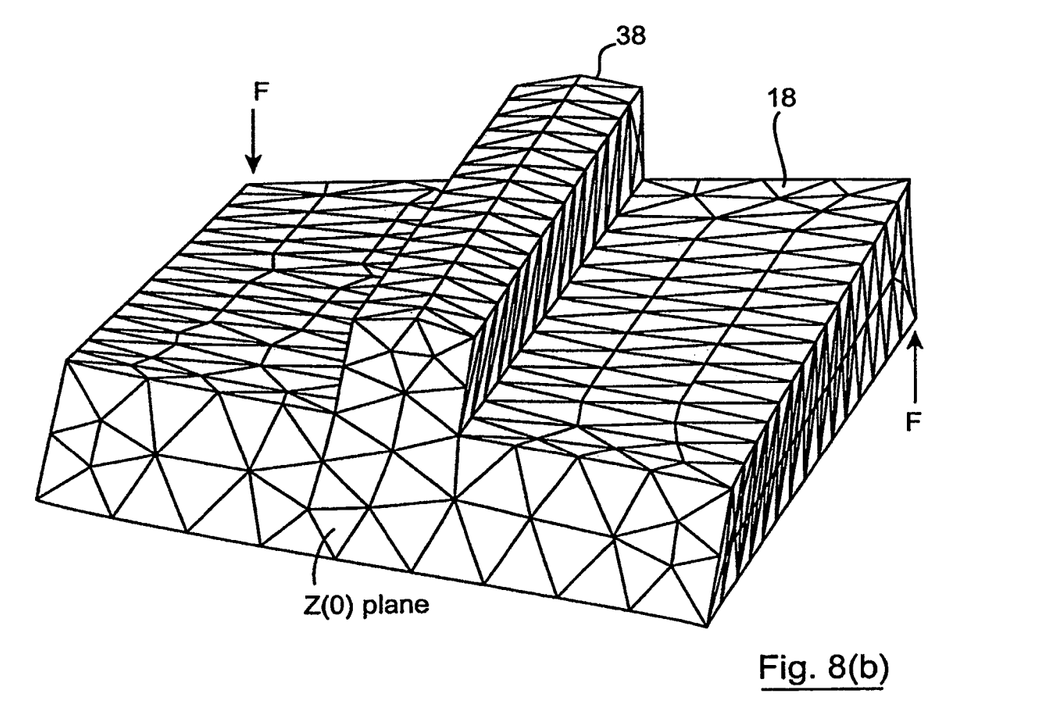

Comparative finite element analysis was carried out on a computer simulated test piece which was of similar transverse cross-section to that of the distal portion 18 of the guide wire 1 with a member similar to the reinforcing member 38. The analysis was also carried out on a computer simulated reference piece, which was also of similar transverse cross-section to that of the distal portion 18, but which was provided without the reinforcing member. The comparative finite element analysis was carded out in order to establish the increase in torsional rigidity provided by one reinforcing member on the distal portion 18 of the guide wire 1. The finite element analysis is described with reference to FIGS. 7 and 8. The reference piece is illustrated in FIGS. 7(a) and 8(a), while the test piece is illustrated in FIGS. 7(b) and 8(b).

In order to investigate the torque responses of the test piece and the reference piece, a Finite Element Analysis Method (FEAM) was, utilised. The reference piece and the test piece were simulated to be of the same material and of equal length, and formed by the same forming process, and of similar lengths. The material of both the test piece and the reference piece was simulated to be 304v stainless steel, with a modulus of elasticity of 210 Gpa and a Poisson's Ratio of 0.3. For modelling purposes, the material was assumed to be linear elastic in behaviour. The reference piece and the test piece were constrained in all degrees of freedom in the end plane (z=0) plane. Simulated forces F were applied to the corners at opposite sides in the vertical y-direction as shown in FIGS.

8(a) and 8(b). The meshes generated by the analysis are illustrated in FIGS. 8(a) and 8(b). The force F applied to the respective opposite sides of the reference piece had a magnitude of 0.01 lbf. In order to have the same moment applied to the test piece as that applied to the reference piece, forces were applied to the respective opposite sides of the test piece with a magnitude of 0.008772 lbf.

The deformed geometry plots for both the reference piece and the test piece when subjected to the loading condition described above are shown in FIGS. 8(a) and 8(b). The y-direction reaction forces on the constrained corner nodes of the unloaded end of each of the reference and the test pieces were investigated. The maximum values of these reaction forces in both the positive and negative y-directions are shown in Table 1 below.

TABLE 1

Maximum values of the y-direction reaction forces at the constrained nodes.

| Force | Uniform cross-section reference piece | Uniform cross-section test piece | Increase in torque response of uniform cross-section test piece |
|---|---|---|---|
| Max. positive y-direction reaction force | 0.94861E−02 | 0.10974E−01 | 15.7% |
| Max. negative y-direction reaction force | −0.94730E−02 | −0.11363E−01 | 20.0% |

From Table 1, it can be seen that the reaction forces, and hence the torque response of the test piece was increased by approximately 15% to 20% over the reference piece, thus significantly enhancing the torsional rigidity of the test piece, and in turn minimising its tendency to axially twist. Thus, the results of the comparative finite element analysis indicate that the provision of the reinforcing member 38 on the distal portion 18 significantly increased the torsional rigidity of the distal portion 18 over and above its torsional rigidity if it were not provided with the reinforcing member 38. Accordingly, the provision of the reinforcing member 38 on the distal portion 18 significantly reduces axial twisting of the distal portion 18 about the central axis 8 as a result of torque induced in the guide wire by rotating the proximal end 5 for in turn rotating the distal tip 9 for alignment with a branched vessel.

Figures 9, 10:
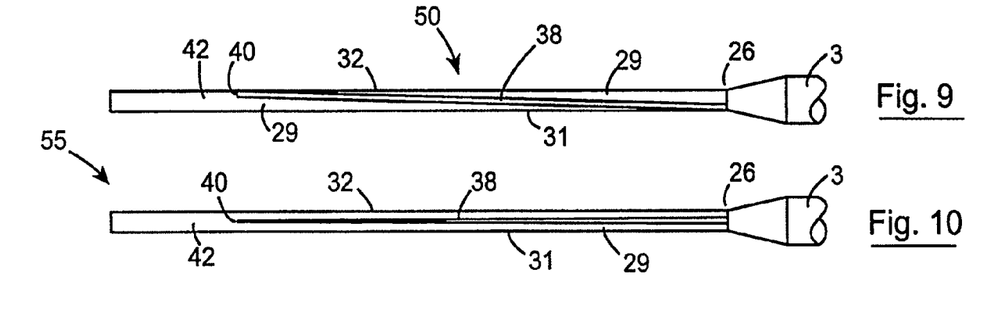
FIGS. 9 and 10 are top plan views of portions of guide wires according to further embodiments of the invention.

Referring now to FIG. 9, there is illustrated a distal portion 50 of a guide wire according to another embodiment of the invention. The guide wire of which the distal portion 50 forms a part is substantially similar to the guide wire 1, and similar components are identified by the same reference numerals. The only difference between the distal portion 50 and the distal portion 18 of the guide wire 1 is that the reinforcing member 38, instead of being located to coincide with the central minor plane 34 of the distal portion 18, in this embodiment of the invention the reinforcing member 38 extends at an angle to the central minor plane 34. The reinforcing member 38 on the major surface 29 extends diagonally from the minor surface 31 adjacent the proximal end 26 to the minor surface 32 adjacent the location 40. A second reinforcing member could be provided on the opposite major surface 30, and could extend at a similar angle to the central minor plane 34, but in the opposite direction.

Referring now to FIG. 10, there is illustrated a distal portion 55 of a guide wire according to another embodiment of the invention. The guide wire of which the distal portion 55 forms a part is similar to the guide wire 1 and similar components are identified by the same reference numerals. The main difference between the distal portion 55 and the distal portion 18 is that in this embodiment of the invention while the reinforcing member 38 coincides with the central minor plane 34, the sides 37 of the reinforcing member 38 converge towards the central major plane 33 adjacent the location 40.

Referring now to FIGS. 11(a) to 11(p), end views of distal portions 60a to 60p are illustrated of guide wires according to other embodiments of the invention. The guide wires of which the distal portions 60a to 60p form part are similar to the guide wire 1 and similar components are identified by the same reference numerals. The distal portions 60a to 60p of the guide wires according to these other embodiments of the invention are views looking in from the distal end of the respective distal portions. As can be seen, different types of reinforcing means are provided on the distal portions 60a to 60p.

In the distal portions of FIGS. 11(a) and (i) the reinforcing means is provided by a reinforcing ridge 61 formed by shaping the distal portion 60. In the distal portion of FIG. 11(j) the reinforcing means is also provided by shaping the distal portion to form a twisted portion 62.

In the distal portion 60 of FIG. 11(b) a pair of reinforcing ridges 63 are provided on the respective opposite major surfaces 29 and 30. Similarly, in the distal portion 60 of FIGS. 11(d), (e), (k), (l), (n) and (o) the reinforcing ridges 63 are provided on the respective opposite major surfaces 29 and 30. The distal portion 60 of FIG. 11(i) is similar to that of FIG. 11(e) with the exception that only a single reinforcing ridge 63 is provided.

In the distal portion 60 of FIG. 11(m) and (p) instead of the reinforcing means being formed by reinforcing ridges, the reinforcing means are provided by increasing the cross-section of the distal portion 60 adjacent the edges defining the minor surfaces 31 and 32.

Figure 11:
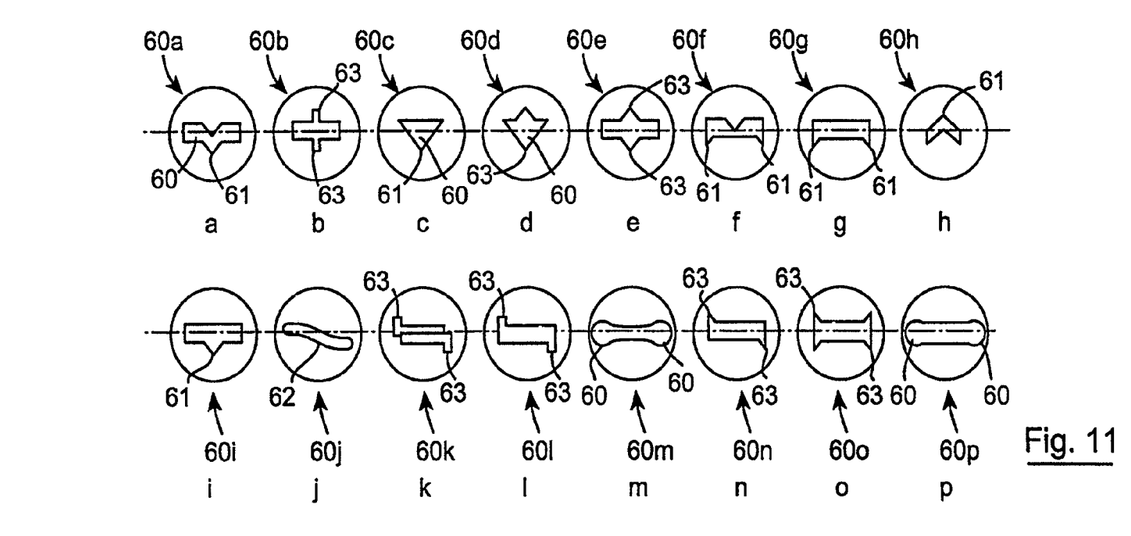

Otherwise the reinforcing means of the distal portion 60 of the remaining distal portion 60 of FIG. 11 are clear from the drawings.

Figures 12, 13:
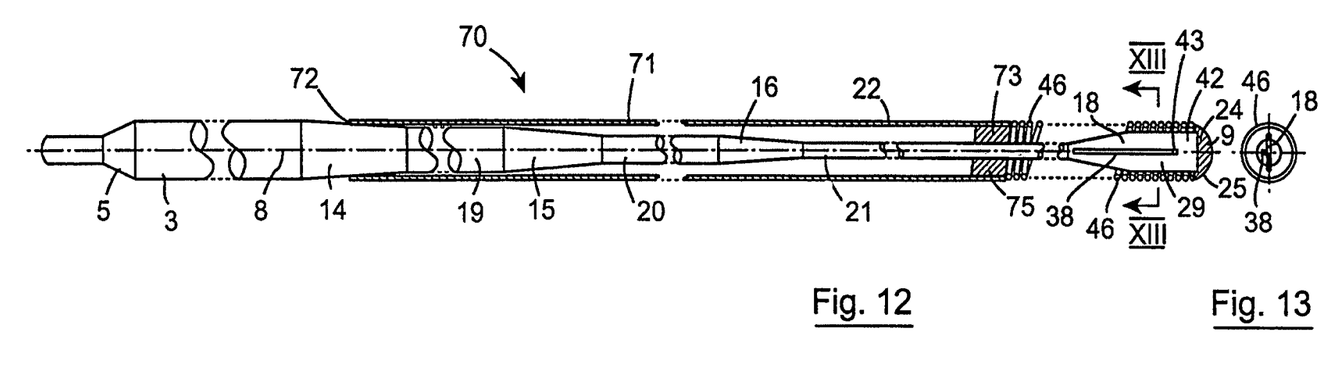
FIG. 12 is a view similar to FIG. 3 of a guide wire according to another embodiment of the invention.
FIG. 13 is a transverse cross-sectional end elevational view of the guide wire of FIG. 12 on the line XIII-XIII of FIG. 12.

Referring now to FIGS. 12 and 13, there is illustrated a guide wire 70 according to another embodiment of the invention. The guide wire 70 is substantially similar to the guide wire 1 and similar components are identified by the same reference numerals. The main difference between the guide wire 70 and the guide wire 1 is in the sleeve 22. In this embodiment of the invention the proximal spring 45 is replaced with a tubular sleeve 71 of plastics material having a proximal end 72 and a distal end 73. The proximal end 72 forms a tight fit on the tapering portion 14, and the distal end 73 of the sleeve 71 is secured to the core wire 3 by an intermediate securing means provided by a securing ring 75 of stainless steel, which is soldered to the core wire 3. The tubular sleeve 71 engages the securing ring 75 with a tight engagement fit. The proximal end of the distal spring 46 is soldered to the securing ring 75 by a solder joint. Otherwise the guide wire 70 is similar to the guide wire 1 and its use is likewise similar to that of the guide wire 1.

Figures 14, 15:
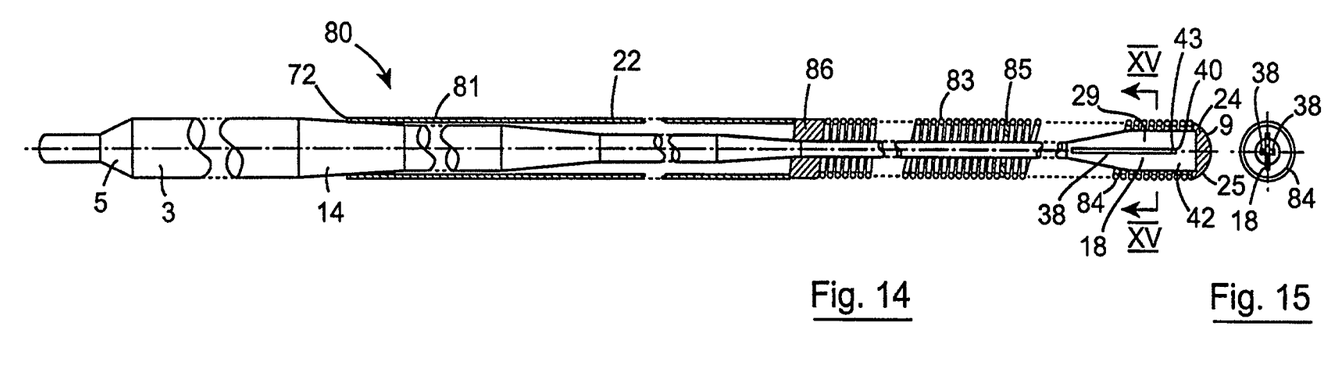
FIG. 14 is a view similar to FIG. 3 of a guide wire according to another embodiment of the invention.
FIG. 15 is a transverse cross-sectional end elevational view of the guide wire of FIG. 14 on the line XV-XV of FIG. 14.

Referring now to FIGS. 14 and 15, there is illustrated a guide wire according to a further embodiment of the invention, indicated generally by the reference numeral 80. The guide wire 80 is substantially similar to the guide wire 1 and similar components are identified by the same reference numerals. In this embodiment of the invention the sleeve 22 is formed by a tubular sleeve 81 of plastics material, which is similar to the tubular sleeve 71 of the guide wire 70, and proximal and distal springs 83 and 84, respectively, which are similar to the proximal and distal springs 45 and 46 of the guide wire 1. The springs 83 and 84 are secured together by an intermediate solder joint 85, similar to the intermediate solder joint 49 of the guide wire 1. The proximal end of the proximal spring 83 is secured to the core wire 3 by an intermediate securing means, provided by a securing ring 86, which is similar to the securing ring 75 of the guide wire 70. The proximal spring 83 is soldered to the securing ring 86, and the tubular sleeve 81 is bonded to the securing ring 86 by an adhesive. Additionally, in this embodiment of the invention a pair of reinforcing members 38 are provided, one reinforcing member 38 being provided on each of the major surfaces 29 and 30. Otherwise, the guide wire 80 is similar to the guide wire 1.

While the guide wires according to the invention have been described for use with a catheter, it is envisaged that in certain cases the guide wires may be used without a catheter, or may be used for other purposes.

Additionally, while the guide wires have been described as comprising a core wire of stainless steel, the core wire may be of any suitable material. Similarly, while it is preferable, it is not essential that the distal portion of the core wire should be integrally formed with the core wire. Similarly, it is not essential that the reinforcing member or members be integrally formed with the distal portion, it or they may be brazed, soldered, welded or otherwise secured onto the distal portion, and in which case, it will be appreciated that the material of the reinforcing member or members may be different to that of the distal portion, and where the distal portion is not integrally formed with the core wire, the distal portion may be of a different material to that of the core wire.

While the guide wire of FIGS. 1 to 6 has been described as comprising one reinforcing member, in certain cases, it is envisaged that a pair of reinforcing members may be provided, one being provided on each of the major surfaces of the distal portion.

While the distal portion has been described as being of flat ribbon-like construction, this is not essential, the distal portion may be of any suitable or desired cross-section.

Needless to say, the sleeve, be it in the form of a spring or of a tubular member, may be of any desired or suitable material. It is also envisaged that in certain cases the sleeve may be provided as a single tubular member, or a pair of tubular members, or a single spring or otherwise, and indeed, in certain cases, it is envisaged that the sleeve in certain embodiments of the invention may be omitted.

While the sleeve has been described as comprising a spring which is soldered to the distal end of the distal portion, the spring may be secured by any other securing means to the distal end of the distal portion, for example, the sleeve, be it a spring or a tubular member of metal or plastics, may be secured to the distal end of the distal portion by an adhesive, such as, for example, an epoxy adhesive, which would similarly be dome shaped. Additionally, instead of soldering, the spring may be secured to the distal end by brazing or welding. Furthermore, the sleeve at its proximal end may terminate at any suitable location along the core wire, and not necessarily at any of the tapered portions.

While the core wire has been described as being tapered over a number of tapering portions with portions of constant diameter in between, while this is preferable, it is not essential, and indeed, the core wire may be tapered over one continuous tapering portion only. It is envisaged that in certain cases, the core wire may not taper towards the distal portion, and in which case it would be of constant diameter to the distal portion.

While the distal portion and the reinforcing member as well as the guide portion have been described as being of specific dimensions, the distal portion, the reinforcing member and the guide portion may be of any other suitable or desired dimensions.

The invention claimed is:

1. A guidewire for use in a surgical or other procedure for accessing a remote site in the body of a human or animal subject, the guide wire defining a longitudinally extending axis, and terminating at one end in a proximal portion, and at an opposite end in a distal portion for accessing the remote site, the distal portion having a proximal end and a distal end, the distal portion being of rectangular transverse cross-section defining a pair of opposite major flat surfaces joined by a pair of opposite minor flat surfaces and terminating in a guide portion, the guide portion being adapted to be shaped to a desired curved configuration for facilitating guiding of the guide wire into a branched vessel of the subject, the guide wire characterized in that a reinforcing member is provided on the distal portion for minimizing axial twisting of the distal portion, the reinforcing member: (i) having a proximal end and a distal end, and a rectangular transverse cross-section with a longitudinally extending edge which converges toward the distal portion adjacent the distal end of the reinforcing member, and (ii) extending along and transversely out from one of the flat major surfaces of the distal portion of the guide wire from the proximal end of the distal portion to a location on the distal portion axially spaced apart from the distal end of the distal portion to define, with the distal end of the distal portion, the guide portion.

* * * * *